(12) United States Patent  
Okaguchi et al.

(10) Patent No.: US 7,762,124 B2  
(45) Date of Patent: Jul. 27, 2010

(54) SENSOR FOR DETECTING SUBSTANCE IN LIQUID

(75) Inventors: Kenjiro Okaguchi, Moriyama (JP); Takuo Hada, Nagaokakyo (JP); Michio Kadota, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 46 days.

(21) Appl. No.: 12/273,657

(22) Filed: Nov. 19, 2008

(65) Prior Publication Data

US 2009/0113997 A1     May 7, 2009

Related U.S. Application Data

(63) Continuation of application No. PCT/JP2007/057164, filed on Mar. 30, 2007.

(30) Foreign Application Priority Data

Jun. 15, 2006    (JP)   ............... 2006-166112

(51) Int. Cl. *G01N 29/02* (2006.01)
(52) U.S. Cl. .................................. 73/61.49
(58) Field of Classification Search ..... 73/54.23–54.27, 73/61.49  
See application file for complete search history.

(56) References Cited

U.S. PATENT DOCUMENTS

| | | | |
|---|---|---|---|
| 4,862,110 A * | 8/1989 | Charbonnier | 331/70 |
| 5,138,869 A * | 8/1992 | Tom | 73/31.03 |
| 5,306,644 A | 4/1994 | Myerholtz et al. | |
| 5,411,709 A * | 5/1995 | Furuki et al. | 422/91 |
| 5,455,475 A * | 10/1995 | Josse et al. | 310/316.01 |
| 6,218,763 B1 * | 4/2001 | Fujimoto et al. | 310/313 R |
| 6,848,295 B2 * | 2/2005 | Auner et al. | 73/24.06 |
| 7,216,962 B2 * | 5/2007 | Miyazawa et al. | 347/68 |

(Continued)

FOREIGN PATENT DOCUMENTS

JP     05-322736 A     12/1993

(Continued)

OTHER PUBLICATIONS

Shiokawa et al.: "Surface Acoustic Wave Sensor for Liquid-Phase Application," 1999 IEEE Ultrasonics Symposium; 1999; vol. 1; pp. 445-452.

(Continued)

*Primary Examiner*—John Fitzgerald  
(74) *Attorney, Agent, or Firm*—Keating & Bennett, LLP

(57) ABSTRACT

A sensor for detecting a substance in liquid includes a sensing oscillation circuit and a reference oscillation circuit. The sensing oscillation circuit includes a sensing SAW element in which a reaction film arranged so as to cover at least one IDT and to react with a substance in liquid is disposed and a first amplifier circuit. The reference oscillation circuit includes a reference SAW element and a second amplifier circuit. The reference SAW element includes at least one IDT and no reaction film. The oscillation frequency of the sensing oscillation circuit and the oscillation frequency of the reference oscillation circuit are separated by at least about $200 \times k^2$ (ppm), where $k^2(\%)$ is the electromechanical coupling coefficient of a piezoelectric substrate used in each of the sensing SAW element and the reference SAW element.

7 Claims, 5 Drawing Sheets

U.S. PATENT DOCUMENTS

| | | | |
|---|---|---|---|
| 7,389,673 | B2 | 6/2008 | Kimura et al. |
| 2009/0060790 | A1* | 3/2009 | Okaguchi et al. .......... 422/68.1 |
| 2009/0061529 | A1* | 3/2009 | Okaguchi et al. .......... 436/150 |

FOREIGN PATENT DOCUMENTS

| | | |
|---|---|---|
| JP | 07-260746 A | 10/1995 |
| JP | 09-080035 A | 3/1997 |
| JP | 3481298 B2 | 12/2003 |
| JP | 3488554 B2 | 1/2004 |
| JP | 2006-47229 A | 2/2006 |
| TW | 200617383 A | 6/2006 |
| WO | 2005/003752 A1 | 1/2005 |
| WO | 2006/027893 A1 | 3/2006 |
| WO | 2006/027945 A1 | 3/2006 |

OTHER PUBLICATIONS

Cunningham et al.: "Design, Fabrication and Vapor Characterization of a Microfabricated Flexural Plate Resonator Sensor and Application to Integrated Sensor Arrays," Sensors and Actuators; 2001; pp. 112-123.

Fadel et al.: "Coupled Determination of Gravimetric and Elastic Effects on Two Resonant Chemical Sensors: Love Wave and Microcantilever Platforms," 2003 IEEE International Frequency Control Symposium and PDA Exhibition Jointly with the 17th European Frequency and Time Forum; 2003; pp. 964-970.

Bender et al.: "Development of a Preconcentration Unit for a Saw Sensor Micro Array and Its Use for Indoor Air Quality Monitoring," Sensors and Actuators; 2003; pp. 135-141.

Kim et al.: "Development of Biosensor Using Surface Acousitc Wave," The 30th Annual Conference of the IEEE Industrial Electronics Society; Nov. 2-6, 2004; pp. 1546-1549.

Kondoh et al : "Identification of Liquid Samples Using SH-SAW Sensors," The Transactions of the Institute of Electronics Information and Communication Engineers; 1995; vol. J78, No. 1; pp. 54-61.

Official Communication issued in International Patent Application No. PCT/JP2007/057164, mailed on Jun. 5, 2007.

Okaguchi et al.; "Sensor for Detecting Substance in Liquid"; U.S. Appl. No. 12/273,569, filed Nov. 19, 2008.

Okaguchi et al.; "Method for Detecting Substance in Liquid and Sensor for Detecting Substance in Liquid"; U.S. Appl. No. 12/273,571, filed Nov. 19, 2008.

Official Communication issued in counterpart Taiwanese Patent Application No. 09920114320, issued on Feb. 23, 2010.

* cited by examiner

SENSOR FOR DETECTING SUBSTANCE IN LIQUID

BACKGROUND OF THE INVENTION

1. Field of the Invention

The present invention relates to sensors for detecting a substance in liquid using a surface acoustic wave element (SAW element), and more specifically, to a sensor for detecting a substance in liquid, the sensor including a sensing SAW element and a reference SAW element.

2. Description of the Related Art

Various sensors have been developed for detecting a substance to be detected (detection-target substance) in liquid, for example, a protein. For example, WO2006/027893A1 listed below discloses a sensor for detecting a substance in liquid using a surface acoustic wave element. FIG. 10A is a plan view of a sensor for detecting a substance in liquid described in WO2006/027893A1, and FIG. 10B is a front cross-sectional view that illustrates a main portion thereof.

A sensor 101 for detecting a substance in liquid includes a base substrate 102. The base substrate 102 includes an upper surface 102a in which recesses 102c and 102d are provided at locations spaced from a first end 102b. A sensing SAW element 104 and a reference SAW element 105 are disposed in the recesses 102c and 102d, respectively. A resin layer 103 having holes 103b and 103c facing the recesses 102c and 102d, respectively, is laminated on the base substrate 102.

The sensing SAW element 104 includes a piezoelectric substrate, an interdigital transducer (IDT) electrode provided on the piezoelectric substrate, and a reaction film arranged so as to cover the IDT electrode. The reaction film is made of a material that reacts with a detection-target substance in liquid and couples to the detection-target substance. The reference SAW element 105 has a configuration in which an IDT electrode is provided on a piezoelectric substrate, and the reference SAW element 105 has no reaction film.

In use, at least the portions in which the holes 103b and 103c are disposed are placed in liquid, and the reaction film of the sensing SAW element 104 reacts with and couples to a detection-target substance. Accordingly, in the sensing SAW element 104, a mass on the portion in which the IDT electrode is disposed is increased by the coupling to the detection-target substance. In contrast, in the reference SAW element 105, because the reaction film that reacts with the detection-target substance is not provided, there is no mass increase caused by the coupling to the detection-target substance.

In the sensor 101 for detecting a substance in liquid described in WO2006/027893A1, a change in the speed of sound of a surface-acoustic wave caused by the addition of mass in the sensing SAW element 104 is detected as a change in an electrical signal. In this case, the detection-target substance is detectable with high precision by determining the difference between an output from the sensing SAW element and an output from the reference SAW element.

A similar sensor for detecting a substance in liquid is also disclosed in WO2006/027945A1.

As described above, the sensor 101 for detecting a substance in liquid detects the presence or absence, and the density of a protein in liquid using the difference between an output signal from the sensing SAW element 104 and that from the reference SAW element 105. In this case, specifically, the difference between an oscillation frequency of an oscillation circuit including the sensing SAW element and that of an oscillation circuit including the reference SAW element is determined to detect the presence or absence or the density of the detection-target substance.

It is desirable for the sensor 101 that, when the detection-target substance is not present, the characteristic of the sensing SAW element 104 and that of the reference SAW element 105 be approximately equal.

However, when the detection-target substance comes into contact with the SAW elements 104 and 105, the difference between the oscillation frequency of the oscillation circuit including the sensing SAW element 104 and that including the reference SAW element 105 may be relatively small. In such a case, both oscillations may be electromagnetically coupled, and both of the oscillation frequencies may be substantially the same. For this reason, it is difficult to detect the detection-target substance in liquid reliably with high precision. Even when both oscillations are not coupled, measurement sensitivity may be relatively small depending on the detection-target substance, and the detection-target substance may be undetectable.

SUMMARY OF THE INVENTION

To overcome the problems described above, preferred embodiments of the present invention provide a sensor for detecting a substance in liquid, the sensor being less prone to problems caused by coupling between the oscillation frequency of an oscillation circuit including a sensing SAW element and including a reference SAW element and being capable of detecting a detection-target substance in liquid with increased sensitivity.

A sensor for detecting a substance in liquid according to a preferred embodiment of the present invention includes a sensing oscillation circuit and a reference oscillation circuit. The sensing oscillation circuit includes a sensing surface acoustic wave (SAW) element and a first amplifier circuit. The sensing SAW element includes a piezoelectric substrate, at least one interdigital transducer (IDT) disposed on the piezoelectric substrate, and a reaction film arranged so as to cover the IDT and to react with a substance in liquid. The first amplifier circuit is connected to the sensing SAW element. The reference oscillation circuit includes a reference SAW element and a second amplifier circuit. The reference SAW element includes a piezoelectric substrate, at least one IDT disposed on the piezoelectric substrate, and not including a reaction film. The second amplifier circuit is connected to the reference SAW element. The piezoelectric substrate of the sensing SAW element and the piezoelectric substrate of the reference SAW element are made of substantially the same piezoelectric material. Where an electromechanical coupling coefficient of each of the piezoelectric substrates is $k^2$(%), an oscillation frequency of the sensing oscillation circuit and an oscillation frequency of the reference oscillation circuit are separated by at least about $200 \times k^2$ (ppm).

In the sensor for detecting a substance in liquid according to preferred embodiments of the present invention, the sensing SAW element and the reference SAW element may preferably have substantially the same frequency characteristic. In this case, because the difference between the characteristic of the sensing SAW element and that of the reference SAW element is relatively small, the detection-target substance in liquid is detectable with greater precision.

In the sensor for detecting a substance in liquid according to preferred embodiments of the present invention, each of the sensing oscillation circuit and the reference oscillation circuit may preferably be an oscillation circuit including a matching circuit defined by an LC circuit, and a circuit constant of the sensing oscillation circuit and a circuit constant of the reference oscillation circuit may preferably be different from one another. That is, by making the circuit constant of the sensing oscillation circuit and that of the reference oscillation circuit different from one another, the oscillation frequency of the sensing oscillation circuit and the oscillation frequency of the reference oscillation circuit is different from each other by at least about 200×$k^2$ (ppm), for example.

In the sensor for detecting a substance in liquid according to preferred embodiments of the present invention, the sensing oscillation circuit may preferably include a first microstrip line, the reference oscillation circuit may preferably include a second microstrip line, and the first and second microstrip lines may have different shapes to separate the oscillation frequency of the sensing oscillation circuit and that of the reference oscillation circuit by the above-described frequency difference. In this case, the oscillation frequency of the sensing oscillation circuit and the oscillation frequency of the reference oscillation circuit can easily be made different from each other by at least about 200×$k^2$ (ppm) merely by selecting the shapes of the microstrip lines.

In the sensor for detecting a substance in liquid according to preferred embodiment of the present invention, a configuration in which the oscillation frequency of the sensing oscillation circuit and that of the reference oscillation circuit are separated by at least about 200×$k^2$ (ppm) may be provided by setting the impedance of a first amplifying element included in the first amplifier circuit and that of a second amplifying element included in the second amplifier circuit to be different from one another.

In preferred embodiments of the present invention, a 30° to 50° rotated Y-plate X-propagation lithium tantalate ($LiTaO_3$) substrate may preferably be used as the piezoelectric substrate. In this case, the presence or absence and the density of the detection-target substance in liquid are detectable with greater precision.

Each of the sensing SAW element and the reference SAW element can be defined by a SAW element that utilizes various surface acoustic waves. Preferably, a SAW element that utilizes surface acoustic waves principally including shear-horizontal (SH) waves may be used. In this case, each of the sensing SAW element and the reference SAW element can be defined by an end-surface reflection surface acoustic wave element. Accordingly, the sizes of the sensing SAW element and the reference SAW element can be reduced.

In the sensor for detecting a substance in liquid according to preferred embodiments of the present invention, because the oscillation frequency of the sensing oscillation circuit and that of the reference oscillation circuit are separated by at least about 200×$k^2$ (ppm), even if variations in the amount of change in frequency when liquid is coupled to the sensing SAW element and the reference SAW element are relatively large, the oscillation of the sensing oscillation circuit and that of the reference oscillation circuit are less prone to being coupled to each other. Accordingly, the presence or absence and the density of a detection-target substance in liquid are detectable with greater sensitivity and reliability based on a change of mass caused by the reaction of the detection-target substance in liquid and the reaction film.

Other features, elements, steps, characteristics and advantages of the present invention will become more apparent from the following detailed description of preferred embodiments of the present invention with reference to the attached drawings.

DETAILED DESCRIPTION OF PREFERRED EMBODIMENTS

Preferred embodiments of the present invention will be described below with reference to the drawings.

Figure 1:
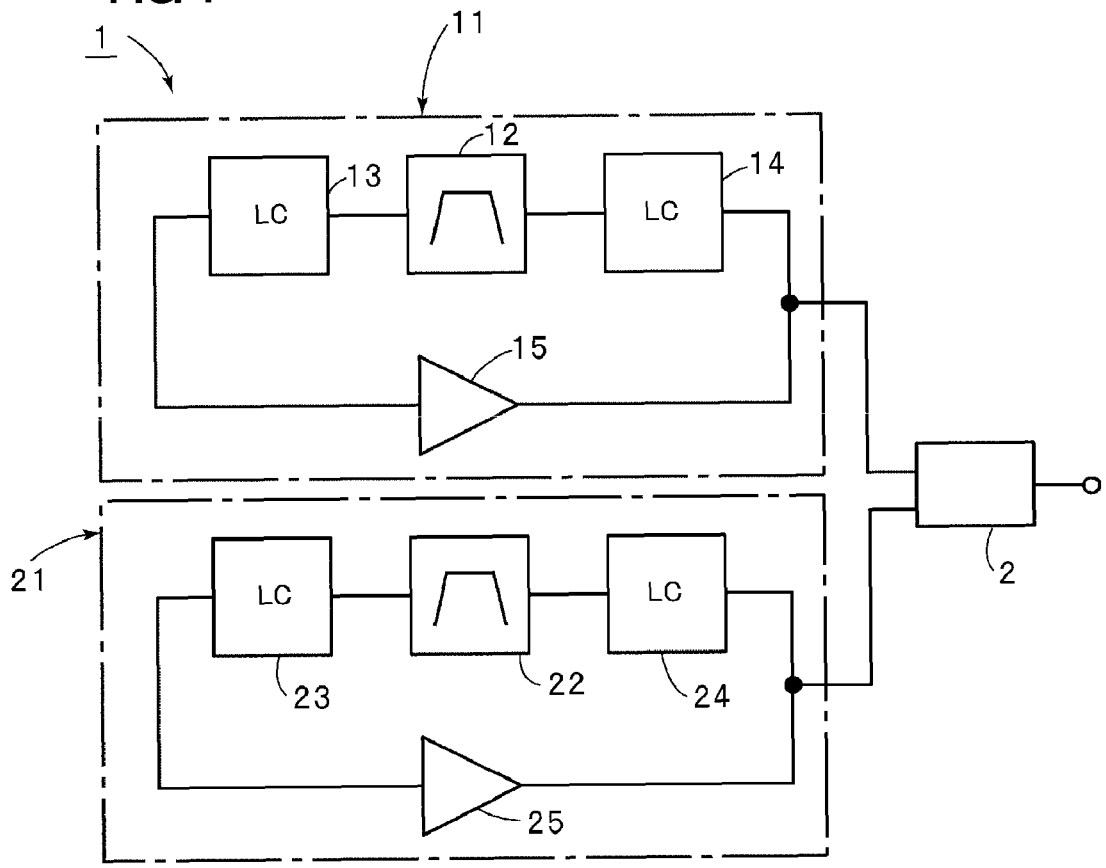
FIG. 1 is a block diagram for describing a sensor for detecting a substance in liquid according to a preferred embodiment of the present invention.

FIG. 1 is a block diagram that illustrates a circuit configuration of a sensor for detecting a substance in liquid according to a preferred embodiment of the present invention. The sensor 1 for detecting a substance in liquid includes a sensing oscillation circuit 11 and a reference oscillation circuit 21.

The sensing oscillation circuit 11 includes a sensing SAW element 12, LC matching circuits 13 and 14 connected to the sensing SAW element 12, and a first amplifier circuit 15. Specifically, in the sensing oscillation circuit, the sensing SAW element 12 is connected to the matching circuits 13 and 14 each defined by an LC circuit and to the first amplifier circuit 15, these components defining a closed-loop oscillation circuit.

Similarly, in the reference oscillation circuit 21, a reference SAW element 22 includes a first end connected to a matching circuit 23 defined by an LC circuit and a second end connected to a matching circuit 24 similarly defined by an LC circuit, and a second amplifier circuit 25 is connected between the matching circuits 23 and 24.

In the sensor 1 for detecting a substance in liquid, the sensing oscillation circuit 11 and the reference oscillation circuit 21 are connected to a differential amplifier circuit 2. Specifically, the sensing oscillation circuit 11 is connected to a first input terminal of the differential amplifier circuit 2 and provides the first input terminal with an output of the sensing oscillation circuit. The reference oscillation circuit 21 is connected to a second input terminal of the differential amplifier circuit 2 so as to provide the second input terminal with an output of the reference oscillation circuit 21. By using the differential amplifier circuit 2, a frequency difference based on the difference between an oscillation frequency of the sensing oscillation circuit and that of the reference oscillation circuit can be obtained.

Figure 2:
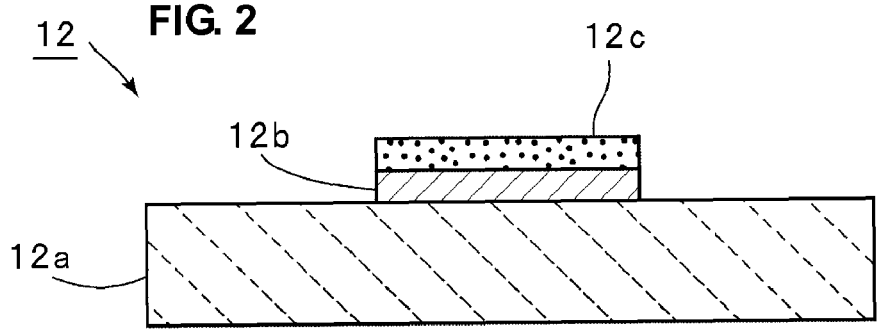
FIG. 2 is a cross-sectional view that schematically illustrates a configuration of a sensing SAW element.
Figure 3:
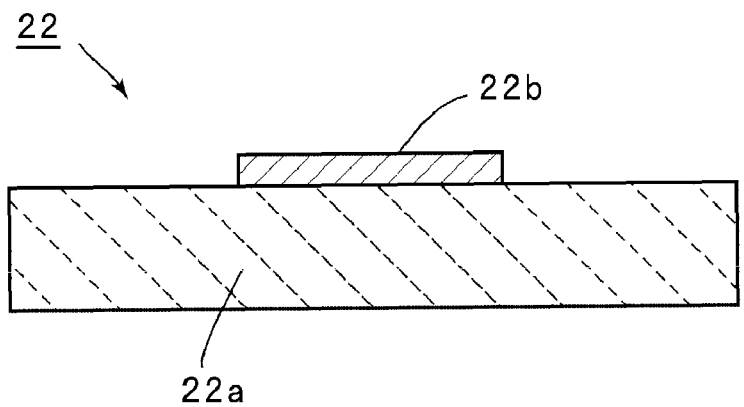
FIG. 3 is a cross-sectional view that schematically illustrates a configuration of a reference SAW element.

Each of the sensing SAW element 12 and the reference SAW element 22 can be defined by a SAW element in which an IDT is provided on a piezoelectric substrate, for example. As schematically illustrated in FIG. 2, in the sensing SAW element 12, an IDT 12b is provided on the upper surface of a piezoelectric substrate 12a, and a reaction film 12c is arranged so as to cover the IDT 12b. In the reference SAW element 22, as schematically illustrated in FIG. 3, an IDT electrode 22b is provided on a piezoelectric substrate 22a. The reference SAW element does not include a reaction film 12c.

FIGS. 2 and 3 illustrate the single IDT 12b in the sensing SAW element 12 and the single IDT 22b in the reference SAW element 22. However, in practice, each of the sensing SAW element 12 and the reference SAW element 22 includes two IDTs arranged in parallel in the direction in which surface acoustic waves travel. In preferred embodiments of the present invention, it is noted that each of the sensing SAW element and the reference SAW element may be a SAW element having a single IDT or may be one having two or more IDTs, as described above.

When the sensing SAW element 12 is arranged in contact with liquid including a detection-target substance, the reaction film 12c reacts with the detection-target substance, and the protein, for example, is coupled to the reaction film 12c. As a result, a mass on each of the IDTs 12b is increased. This increased mass changes an output frequency of the sensing oscillation circuit 11. The presence or absence or the density of the detection-target substance is measured based on the change in the output frequency.

The reaction film 12c is preferably made of a suitable material that can react with a detection-target substance in liquid. For example, to measure an antigen or antibody in liquid, a film in which the antigen or antibody is immobilized can be used as the reaction film. In this case, the antigen or antibody in liquid is coupled to the antigen or antibody immobilized in the reaction film, and an immune complex is thus formed. This formation varies a mass on the portion in which the IDT is disposed. Such a reaction film made of a suitable material that reacts with a detection-target substance in liquid and varies a mass on the portion in which the IDT is disposed can be selected as the reaction film 12c depending on the properties of the detection-target substance. The detection-target substance is not limited to an antigen and antibody and can be various biochemical materials, including a protein. In addition, the detection-target substance is not limited to such biochemical materials. Various elements and inorganic compounds can be a target material to be detected. That is, the sensor for detecting a substance in liquid according to preferred embodiments of the present invention is suitable for use as a biosensor for detecting a biogenic substance, such as an antigen, antibody, or protein. However, it is not limited to the biosensor and can also be used for detecting various substances.

To remove noise caused by a change in temperature, the reference oscillation circuit 21 including the reference SAW element 22 is also provided. That is, background noise and noise caused by a change in temperature are removed by subtracting a result obtained in the reference oscillation circuit 21 from a result obtained in the sensing oscillation circuit 11. Accordingly, the presence or absence and the density of a detection-target substance can be accurately detected.

In addition, in the sensor 1 for detecting a substance in liquid according to the present preferred embodiment, the oscillation frequency of the above sensing oscillation circuit 11 and that of the reference oscillation circuit 21 are preferably separated by at least about $200 \times k^2$ (ppm), for example, where $k^2$ is the electromechanical coupling coefficient of the piezoelectric substrate included in each of the sensing SAW element 12 and the reference SAW element 22. It is noted that the sensing SAW element 12 and the reference SAW element 22 are provided as different chip components. The piezoelectric substrate and the IDT electrodes of the sensing SAW element and those of the reference SAW element are substantially the same, respectively.

In the present preferred embodiment, as described above, the oscillation frequency of the sensing oscillation circuit and that of the reference SAW element are preferably separated by at least about $200 \times k^2$ (ppm), for example. Thus, the quality of a substance in liquid can be measured with greater sensitivity and reliability. This will be described in more detail below.

Figure 4:
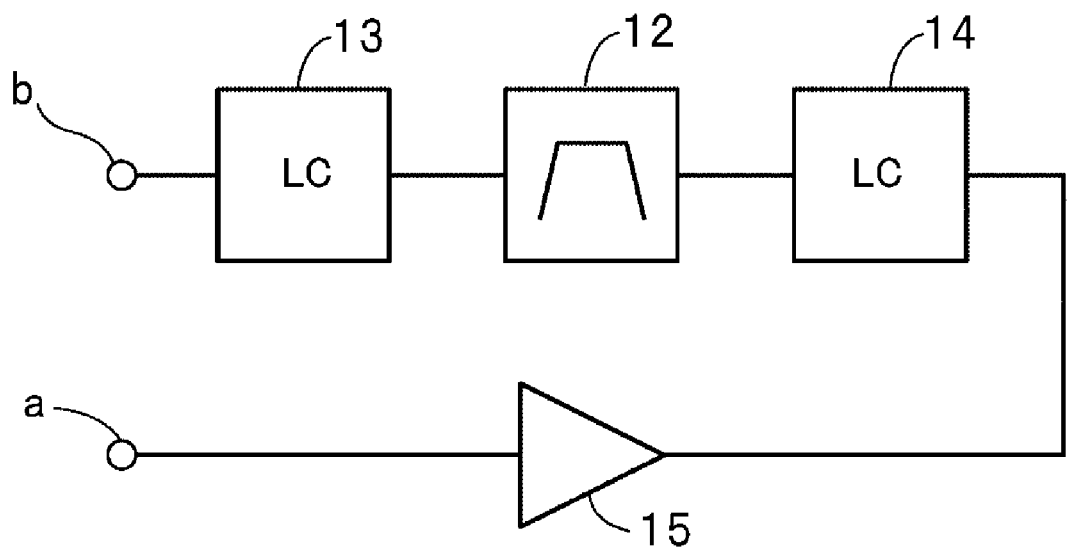
FIG. 4 is a circuit diagram that illustrates an open-loop circuit model for describing the oscillation of a sensing oscillation circuit according to a preferred embodiment of the present invention.

An oscillation of the sensing oscillation circuit 11 is discussed using the open-loop circuit illustrated in FIG. 4 as a model.

The open-loop circuit illustrated in FIG. 4 includes ports a and b. In this open-loop circuit, from the port a toward the port b, the first amplifier circuit 15, the matching circuit 14, the sensing SAW element 12, and the matching circuit 13 are connected in series in this order. Conditions for oscillating this open-loop circuit are satisfied by the following expressions (1) and (2).

Amplitude Condition $$|Sab| \geq 0 (dB) \quad (1)$$

Shift Condition $$\angle Sab = 360 \times n (\text{deg}) \quad (2)$$

where n is an integer.

That is, to make the circuit oscillate, it is necessary to set a circuit constant of the sensing oscillation circuit 11 at a value at which the loop gain is at least about 0 dB and the phase shift is about 0. Examples of the circuit constant include a value in which the amplification factor of the amplifier circuit 15 or the inductance L or the capacitance C in the matching circuit 13 or 14 is adjusted. By selecting this circuit constant, that is, by setting the circuit constant so as to satisfy the expressions (1) and (2), the sensing oscillation circuit 11 can be oscillated, and the oscillation frequency thereof can be set.

For example, when a 36° Y-cut X-propagation lithium tantalate ($LiTaO_3$) substrate is used as the piezoelectric substrate, the value of the inductance L or the capacitance C may be adjusted such that the expressions (1) and (2) are satisfied and such that the oscillation frequency of the sensing oscillation circuit 11 is less than that of the reference oscillation circuit 21. That is, by adjusting the value of the inductance component L or the value of the capacitance component C of the matching circuit 13 or 14, the oscillation frequency of the sensing oscillation circuit 11 in an initial state in which a detection-target substance is not coupled to the reaction film can be set to be less than the oscillation frequency of the reference oscillation circuit 21, as described above. By setting the difference between the oscillation frequency of the sensing oscillation circuit 11 and that of the reference oscillation circuit 21 at least about 1000 ppm, both of the oscillations can be prevented from being coupled, such that measurement can be performed with increased precision.

It is noted that the electromechanical coupling coefficient $k^2$(%) of the 36° Y-cut X-propagation LiTaO$_3$ is preferably about 5.0 (%). Accordingly, at least about 1000 ppm satisfies the range of at least about $200 \times k^2$ (ppm).

Figure 5:
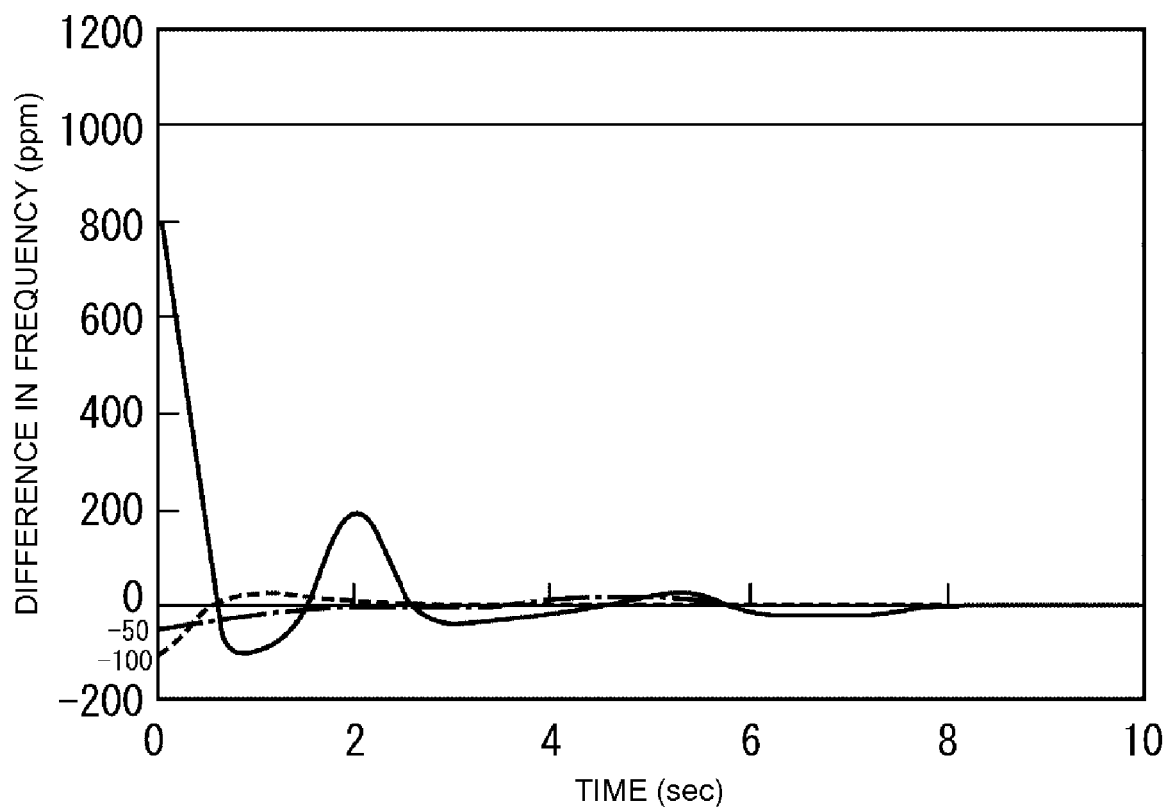
FIG. 5 illustrates a change with time of the frequency difference between oscillation circuits of a sensor for detecting a substance in liquid according to a preferred embodiment of the present invention and of sensors for detecting a substance in liquid prepared for comparison having frequency differences of about −100 ppm, about −50 ppm, about +800 ppm, and about 1000 ppm.

That is, as illustrated in FIG. 5, a plurality of types of sensors for detecting a substance in liquid were produced in which the circuit constant of each of the sensing oscillation circuit 11 and the reference oscillation circuit 21 was adjusted such that the difference in oscillation frequency between the oscillation circuits was about −100 ppm, about −50 ppm, about +800 ppm, or about +1000 ppm in an initial state. These sensors for detecting a substance in liquid were disposed in phosphate buffered saline (PBS) as a sample. This sample is liquid that does not include a detection-target substance. As shown in FIG. 5, when the frequency difference is about −100 ppm, about −50 ppm, and about +800 ppm, the frequency difference disappears with a lapse of time, that is, it disappears within about 10 seconds. In contrast, when the oscillation frequency of the sensing oscillation circuit 11 and the oscillation frequency of the reference oscillation circuit in an initial state is about 1000 ppm, the frequency difference is substantially constant and does not substantially decreased with the lapse of time. This is because the oscillation frequency of the sensing oscillation circuit 11 and that of the reference oscillation circuit 21 are sufficiently separated and are not coupled to one another. That is, when the frequency difference between the oscillation circuits is less than about 1000 ppm, as is clear from FIG. 5, the oscillation of the sensing oscillation circuit 11 and that of the reference oscillation circuit 21 are coupled to each other with a lapse of time, and the frequency difference therebetween disappears.

The electromechanical coupling coefficient and the bandwidth are proportional to each other. Accordingly, when the frequency difference at which no coupling occurs is df, when the electromechanical coupling coefficient of the piezoelectric substrate is $k^2$(%), df (ppm) can be set at a value substantially equal to or greater than the electromechanical coupling coefficient $k^2 \times A$ (ppm), where A is a constant of a comparison example, and, from the results of FIG. 5, df$\geq k^2 \times 200$ (ppm) is satisfied. That is, with the 36° Y-cut X-propagation LiTaO$_3$ substrate, the electromechanical coupling coefficient $k^2$ is about 5.0%, and, from the results of FIG. 5, the difference df between the oscillation frequency of the sensing oscillation circuit 11 and that of the reference oscillation circuit 21 can be set to be at least about 1000 ppm. From these results, it is determined that, when df$\geq k^2 \times 200$ (ppm), coupling between the oscillation of the reference oscillation circuit and that of the sensing oscillation circuit can be prevented, and thus, a substance in liquid can be detected with greater reliability. This will be described more specifically with reference to FIGS. 6 to 8.

Figure 8:
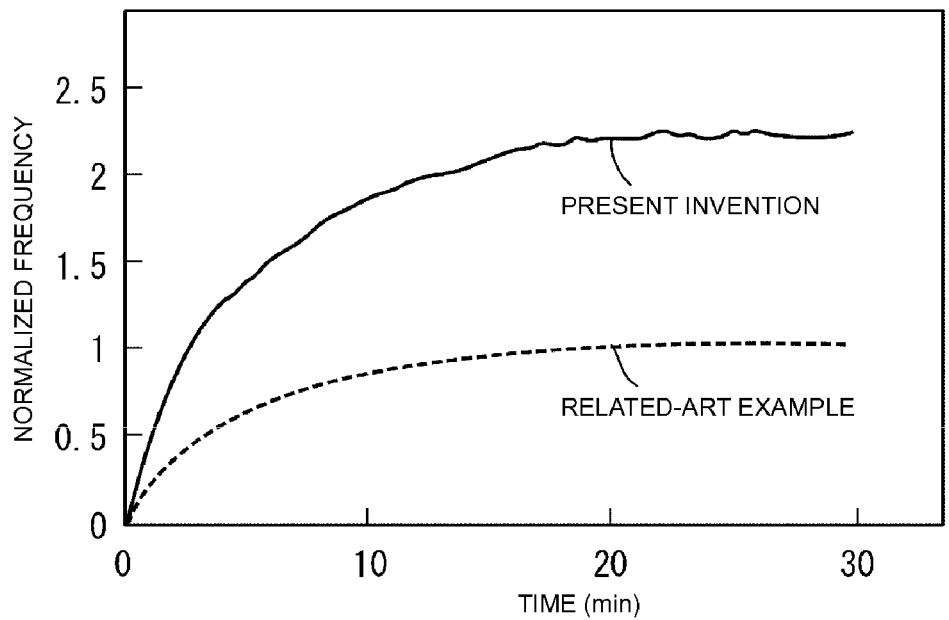
FIG. 8 illustrates a change with time in the sensitivity of a sensor for detecting a substance in liquid according to a preferred embodiment of the present invention and that according to a related art example.

The above sensor 1 for detecting a substance in liquid configured such that df is about 1320 ppm and a sensor for detecting a substance in liquid configured such that df is about 570 ppm in a related art example for comparison were prepared, PBS was prepared as a sample, and measurements were performed. FIG. 8 illustrates a change in sensitivity with time when the sensor for detecting a substance in liquid in the above-described preferred embodiment and that in the related art were used. In FIG. 8, the vertical axis represents the normalized frequency corresponding to the sensitivity and the horizontal axis represents the time.

As shown in FIG. 8, the present preferred embodiment can detect a substance with greater sensitivity, as compared to the related art example, because the oscillation frequency of the sensing oscillation circuit 11 and that of the reference oscillation circuit 21 are different from one another.

Figure 6:
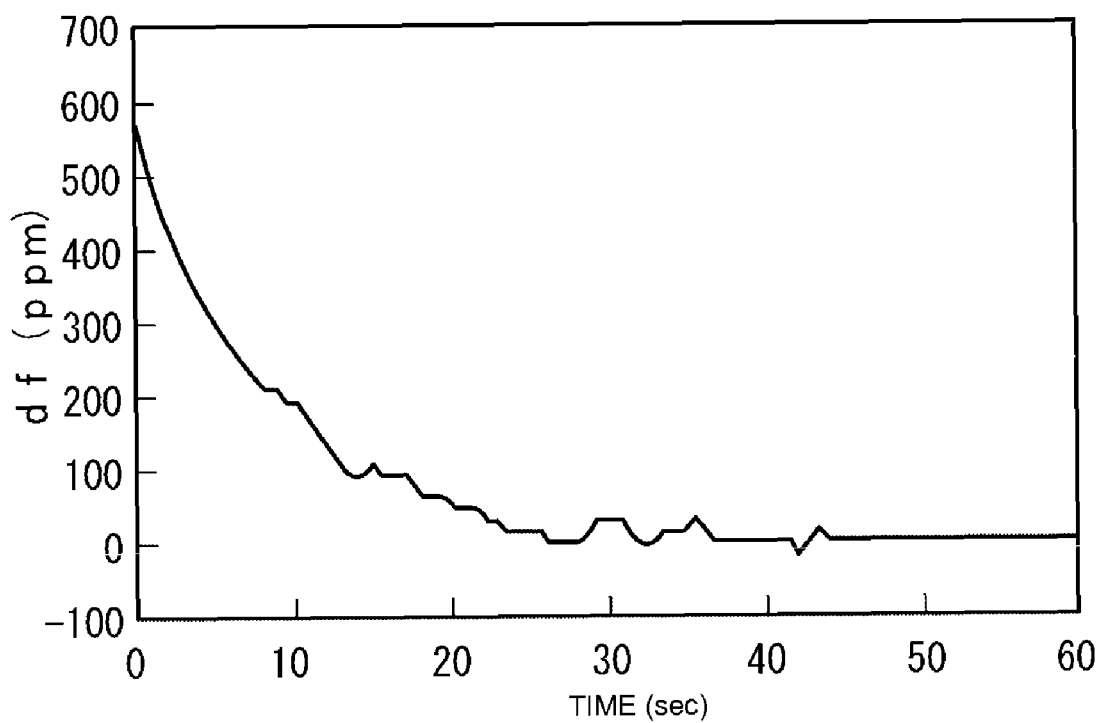
FIG. 6 illustrates a change with time of the frequency difference between both oscillation circuits of a sensor for detecting a substance in liquid prepared for comparison having a frequency difference of about 570 ppm.
Figure 7:
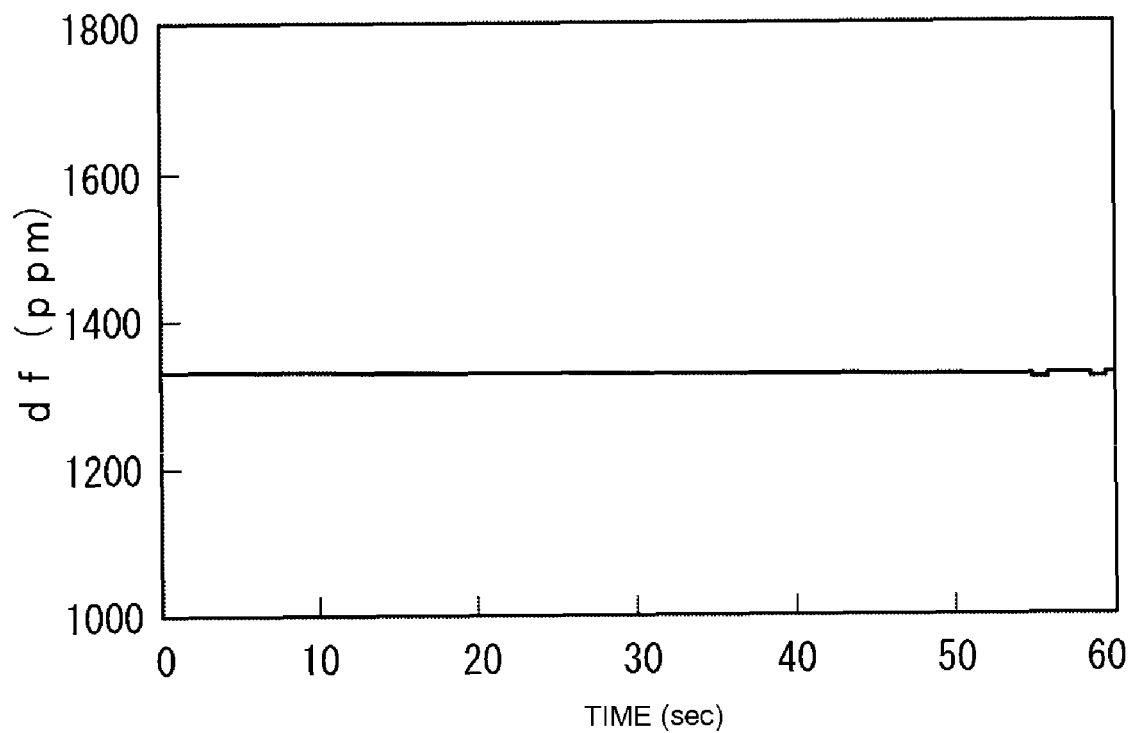
FIG. 7 illustrates a change with time of the frequency difference between the sensing oscillation circuit and the reference oscillation circuit of a sensor for detecting a substance in liquid according to a preferred embodiment of the present invention having a frequency difference of about 1320 ppm.

FIG. 6 illustrates a change with time of the frequency difference, df, between the sensing oscillation circuit 11 and the reference oscillation circuit 21 in the related art example. FIG. 7 illustrates a change with time of the frequency difference, df, in the sensor for detecting a substance in liquid in the present preferred embodiment. As shown in FIG. 6, in the related art example, the frequency difference is substantially zero after a lapse of about 30 seconds. In contrast, in the present preferred embodiment illustrated in FIG. 7, the frequency difference is constant at about 1320 ppm/° C.

Accordingly, the sensor for detecting a substance in liquid according to the present preferred embodiment can detect the presence or absence and the density of a substance in liquid with greater sensitivity and reliability because the oscillation of the sensing oscillation circuit 11 and that of the reference oscillation circuit 21 are less prone to being electromagnetically coupled to each other.

The oscillation frequency of each of the sensing oscillation circuit 11 and the reference oscillation circuit 21 can be adjusted using various methods, such as adjusting L or C of the matching circuit, as previously described, inserting a resistance R, changing a wire length of a connection between circuit components, a line width, or a gap to the ground potential, or controlling a feedback capacitance of an IC using an electric power, for example.

Figure 9:
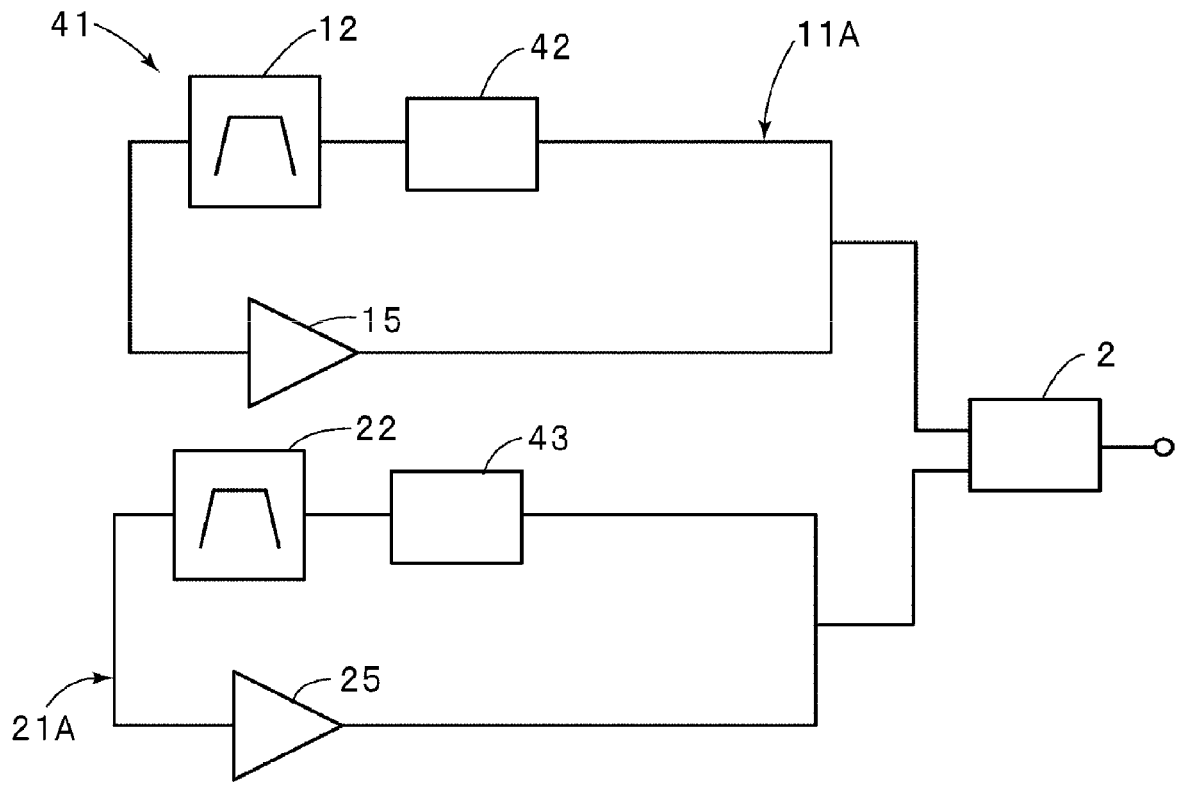
FIG. 9 is a block diagram of a sensor for detecting a substance in liquid according to a modified example of a preferred embodiment according to the present invention in which each of a sensing oscillation circuit and a reference oscillation circuit includes a microstrip line.
Figure 10A:
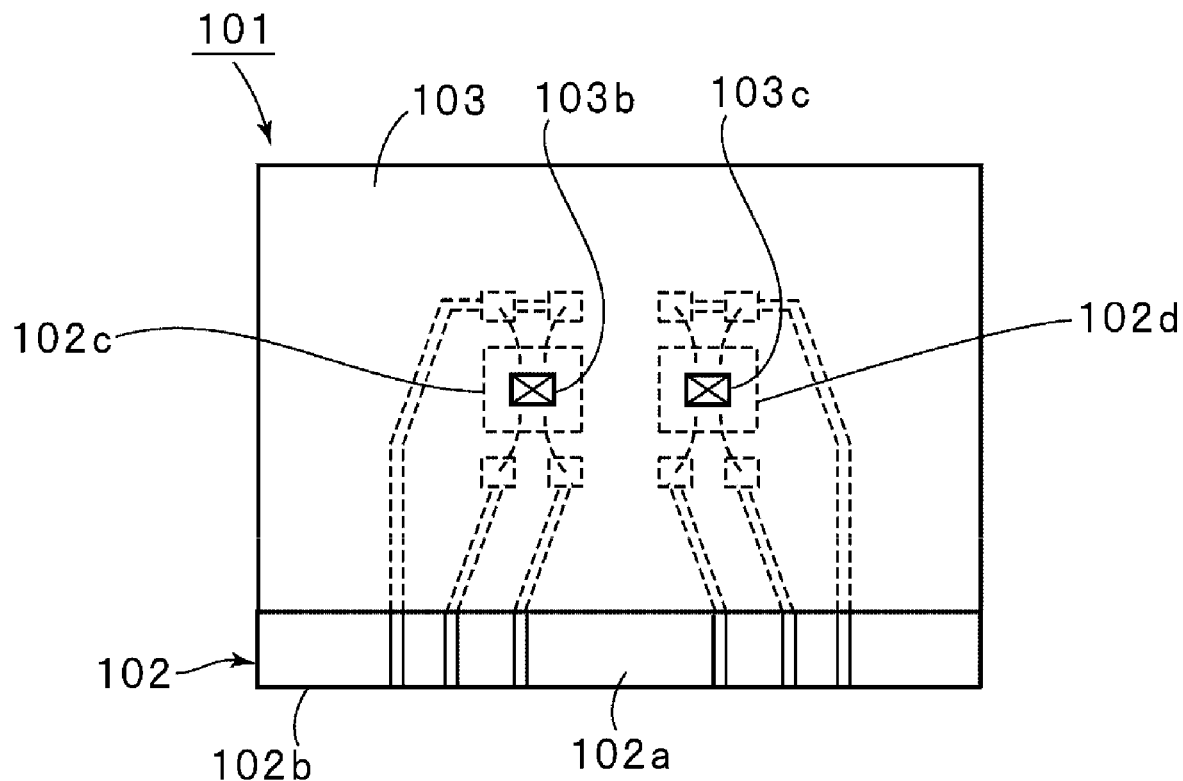
FIG. 10A is a plan view that illustrates one example of a known sensor for detecting a substance in liquid.
Figure 10B:
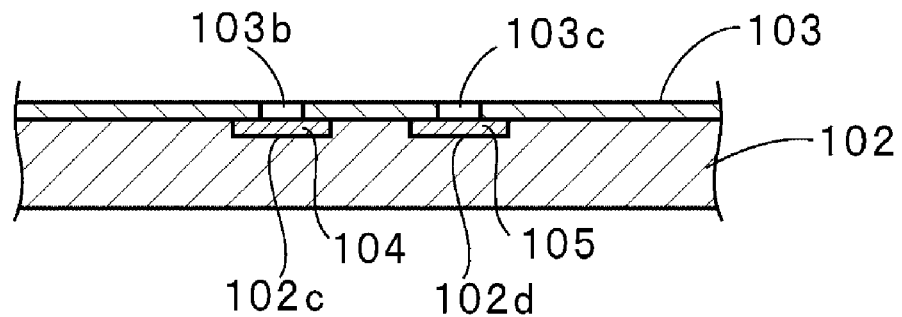
FIG. 10B is a front cross-sectional view that illustrates a main portion thereof.

As in a sensor 41 for detecting a substance in liquid according to a modified example according to a preferred embodiment of the present invention, which is schematically illustrated in FIG. 9, a sensing oscillation circuit 11A may preferably include a first microstrip line 42, and a reference oscillation circuit 21A may preferably include a second microstrip line 43. In this case, the separation of the oscillation frequency of the sensing oscillation circuit 11A and that of the reference oscillation circuit by at least about $200 \times k^2$ (ppm) is preferably achieved by making the shape of the first microstrip line 42 and that of the second microstrip line 43 different in width, in length, and/or in other characteristics.

The first and second amplifier circuits 15 and 25 may preferably include first and second amplifying elements, respectively. The separation of the oscillation frequency of the sensing oscillation circuit 11 and that of the reference oscillation circuit by at least about $200 \times k^2$ (ppm) can preferably be provided by making the impedance of the first amplifying element and that of the second amplifying element different from one another.

In the preferred embodiment described above, the 36° Y-cut X-propagation LiTaO$_3$ substrate is preferably used as the piezoelectric substrate. However, the piezoelectric substrate is not limited to that substrate. For example, the piezoelectric substrate may be made of a suitable piezoelectric single crystal, such as a LiTaO$_3$ substrate of another crystal orientation, or a lithium niobate (LiNbO$_3$) substrate, or piezoelectric ceramic. Preferably, a 30° to 40° Y-cut X-propagation LiTaO$_3$ substrate may be used, which enables a detection-target substance in liquid to be detected with improved sensitivity and reliability.

The SAW elements used in the above-described preferred embodiments are not limited to a particular type of SAW element. SAW elements that utilize various types of surface acoustic waves, such as Rayleigh waves or shear-horizontal (SH) waves, can be used, for example. If surface acoustic waves including primarily of SH waves are used, an endsurface-reflection SAW device can be provided. As a result, the size of the sensor for detecting a substance in liquid can be reduced.

Each of the above SAW elements can also be a SAW resonator or a SAW filter, for example.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A sensor for detecting a substance in liquid, the sensor comprising:
a sensing oscillation circuit including a sensing surface acoustic wave element and a first amplifier circuit, the sensing surface acoustic wave element including a piezoelectric substrate, at least one interdigital transducer disposed on the piezoelectric substrate, and a reaction film arranged so as to cover the interdigital transducer and to react with a substance in liquid, the first amplifier circuit being connected to the sensing surface acoustic wave element; and
a reference oscillation circuit including a reference surface acoustic wave element and a second amplifier circuit, the reference surface acoustic wave element including a piezoelectric substrate, at least one interdigital transducer disposed on the piezoelectric substrate, and including no reaction film, the second amplifier circuit being connected to the reference surface acoustic wave element; wherein
the piezoelectric substrate of the sensing surface acoustic wave element and the piezoelectric substrate of the reference surface acoustic wave element are made of substantially the same piezoelectric material, and, where an electromechanical coupling coefficient of each of the piezoelectric substrates is $k^2$, an oscillation frequency of the sensing oscillation circuit and an oscillation frequency of the reference oscillation circuit are separated by at least about $200 \times k^2$.

2. The sensor for detecting a substance in liquid according to claim 1, wherein the sensing surface acoustic wave element and the reference surface acoustic wave element have substantially the same frequency characteristic.

3. The sensor for detecting a substance in liquid according to claim 1, wherein each of the sensing oscillation circuit and the reference oscillation circuit is an oscillation circuit including a matching circuit defined by an LC circuit, and a circuit constant of the sensing oscillation circuit and a circuit constant of the reference oscillation circuit are different from one another.

4. The sensor for detecting a substance in liquid according to claim 1, wherein the sensing oscillation circuit includes a first microstrip line, the reference oscillation circuit includes a second microstrip line, and the first and second microstrip lines have different shapes.

5. The sensor for detecting a substance in liquid according to claim 1, wherein the first amplifier circuit and the second amplifier circuit include a first amplifying element and a second amplifying element, respectively, and an impedance of the first amplifying element and an impedance of the second amplifying element are different from one another.

6. The sensor for detecting a substance in liquid according to claim 1, wherein the piezoelectric substrate is a 30° to 50° rotated Y-plate X-propagation lithium tantalate substrate.

7. The sensor for detecting a substance in liquid according to claim 1, wherein each of the sensing surface acoustic wave element and the reference surface acoustic wave element is a surface acoustic wave element that utilizes surface acoustic waves primarily including shear-horizontal waves.

* * * * *